United States Patent
Zhang et al.

(10) Patent No.: US 8,642,260 B2
(45) Date of Patent: Feb. 4, 2014

(54) SINGLE QUANTUM-DOT BASED APTAMERIC NANOSENSORS

(75) Inventors: Chun-yang Zhang, Flushing, NY (US); Lawrence W. Johnson, Hastings-on-Hudson, NY (US)

(73) Assignee: The Research Foundation of the City University of New York, New York, NY (US)

( * ) Notice: Subject to any disclaimer, the term of this patent is extended or adjusted under 35 U.S.C. 154(b) by 157 days.

(21) Appl. No.: 13/124,356

(22) PCT Filed: Oct. 21, 2009

(86) PCT No.: PCT/US2009/005737
§ 371 (c)(1),
(2), (4) Date: Jun. 27, 2011

(87) PCT Pub. No.: WO2010/047797
PCT Pub. Date: Apr. 29, 2010

(65) Prior Publication Data
US 2011/0287557 A1  Nov. 24, 2011

Related U.S. Application Data

(60) Provisional application No. 61/107,109, filed on Oct. 21, 2008.

(51) Int. Cl.
*C12Q 1/68* (2006.01)
*C07H 21/00* (2006.01)
*C07H 21/02* (2006.01)
*C07H 21/04* (2006.01)

(52) U.S. Cl.
USPC .......... 435/6.1; 536/22.1; 536/23.1; 536/24.3

(58) Field of Classification Search
USPC .............. 435/6.1, 283.1; 536/22.1, 23.1, 24.3
See application file for complete search history.

(56) References Cited

U.S. PATENT DOCUMENTS

| | | | |
|---|---|---|---|
| 7,332,283 B2 | 2/2008 | Lu et al. | |
| 2004/0219523 A1 | 11/2004 | Stanton et al. | |
| 2007/0042431 A1* | 2/2007 | Urdea et al. | 435/7.1 |
| 2007/0269821 A1 | 11/2007 | Mazumdar et al. | |

OTHER PUBLICATIONS

Liu et al., J. Am. Chem. Soc. 2007, 129, 8634-8643. (Abstract Only).
Stojanovic et al., J. Am. Chem. Soc. 2002, 124, 9678-9679. (Abstract Only).
Liu et al., Anal. Chem. 2007, 79, 4120-4125. (Abstract Only).

(Continued)

*Primary Examiner* — Ethan C Whisenant
(74) *Attorney, Agent, or Firm* — Hoffmann & Baron, LLP

(57) ABSTRACT

A signal-off-quantum-dot-based sensor for detecting the presence of a target molecule comprising: an aptamer probe having a nucleotide sequence which specifically interacts with the target molecule by sequence-dependent interaction, wherein the aptamer probe is sandwiched between (a) an oligonucleotide which is immobilized on the surface of a quantum dot (QD), and (b) a fluorophore-labeled oligonucleotide, wherein when the sensor is excited by an energy source: (i) in the absence of specific interaction between the target molecule and the aptamer probe, a baseline signal is emitted, and (ii) in the presence of specific interaction between the target molecule and the aptamer probe, a detection signal is emitted, wherein the baseline signal is greater than the detection signal, whereby the presence of the target molecule is detected.

16 Claims, 8 Drawing Sheets

(56) References Cited

OTHER PUBLICATIONS

Chen et al., Anal. Bioanal. Chem. 2008, 392:1185-1188.

Levy et al., ChemBio 2005, 6:2163-2166.

Stojanovic et al., J. Am. Chem. Soc. 2001, 123, 4928-4931. (Abstract Only).

* cited by examiner

US 8,642,260 B2

SINGLE QUANTUM-DOT BASED APTAMERIC NANOSENSORS

CROSS-REFERENCE TO RELATED APPLICATION

This application is the U.S. National Phase of, and claims priority to, International Patent Application Number PCT/US2009/005737 filed 21 Oct. 2009, which claims the benefit of U.S. Provisional Application No. 61/107,109, filed Oct. 21, 2008, which is incorporated herein by reference in its entirety.

BACKGROUND OF THE INVENTION

Sensitive detection of biological and chemical species is important in various fields, such as, for example, forensic analysis, environmental monitoring and clinic diagnostics. For instance, sensitive detection of cocaine may be critical for law enforcement and clinical diagnostics.

Aptamers have been developed to detect a variety of molecular targets including, for example, small molecules, nucleic acids, proteins and cancer cells. Aptamers are oligonucleotides with ligand-binding ability.

Various aptamer sensors based on colorimetric, electrochemistric and bulk fluorescence assay have been developed for several targets, including for cocaine detection. (Liu et al., *J. Am. Chem. Soc.* 2007, 129, 8634-8643; Liu et al., *J. Angew. Chem. Int. Ed.* 2006, 45, 90-94; Stojanovic et al., *J. Am. Chem. Soc.* 2002, 124, 9678-9679; Baker et al., *J. Am. Chem. Soc.* 2006, 128, 3138-3139; Stojanovic et al., *J. Am. Chem. Soc.* 2001, 123, 4928-4931; Stojanovic et al., *J. Am. Chem. Soc.* 2000, 122, 11547-11548; Shlyahovsky et al., *J. Am. Chem. Soc.* 2007, 12,3814-3815; and Liu et al., *Anal. Chem.* 2007, 79, 4120-4125.)

However, reported aptamer sensors either exhibit relatively low detection limits, or low detection sensitivity, or involve complicated sample preparation and large sample consumption. Accordingly, there is a need for simple and sensitive detection methods using aptamer sensors.

SUMMARY OF THE INVENTION

In one embodiment, the invention is a signal-off-quantum-dot-based sensor for detecting the presence of a target entity comprising: an aptamer probe having a nucleotide sequence which specifically interacts with the target entity, wherein the aptamer probe is sandwiched between (a) a tagged-oligonucleotide which is capable of being immobilized on the surface of a quantum dot (QD), and (b) an oligonucleotide labeled with a fluorophore, designated as "FP-oligonucleotide," wherein when the sensor is excited by an energy source: (i) in the absence of specific interaction between the target entity and the aptamer probe, a baseline signal is emitted, and (ii) in the presence of specific interaction between the target entity and the aptamer probe, a detection signal is emitted, wherein the baseline signal is greater than the detection signal, whereby the presence of the target entity is detected. In the sandwich hybrid, preferably, the "FP-oligonucleotide" and the tagged-oligonucleotide are hybridized to opposite sides of the aptamer probe.

The aptamer probe comprises an aptamer and an attached tail sequence, wherein the tail sequence comprises two separate parts designated as "$1^{st}$ part of tail" and "$2^{nd}$ part of tail," wherein a portion of the "FP-oligonucleotide" is hybridized to the "$1^{st}$ part of tail," and wherein the tagged-oligonucleotide, or a portion thereof, is hybridized to the "$2^{nd}$ part of tail." The aptamer probe comprises a spacer nucleotide sequence between the "$1^{st}$ part of tail" and the "$2^{nd}$ part of tail." A portion of the "FP-oligonucleotide" is hybridized to the "$1^{st}$ part of tail," and a portion of the "FP-oligonucleotide" is hybridized to the aptamer, wherein the "FP-oligonucleotide" disassociates from the sensor when the aptamer attaches to the target entity. Preferably, about 50% of "FP-oligonucleotide" is hybridized to the "$1^{st}$ part of tail"; and about 50% of the "FP-oligonucleotide" is hybridized to the aptamer. The tagged-oligonucleotide is immobilized on the surface of a QD by binding of a tag on the tagged-oligonucleotide, wherein the distance between the fluorophore and the QD allows FRET.

In another embodiment, the invention is a signal-on-quantum-dot-based sensor for detecting the presence of a target entity comprising: an aptamer probe having a nucleotide sequence which specifically interacts with the target molecule, wherein the aptamer probe is sandwiched between (a) a quencher-labeled oligonucleotide; and (b) an oligonucleotide which is tagged and labeled with a fluorophore, designated as "tagged-FP-oligonucleotide," wherein the "tagged-FP-oligonucleotide" is capable of being immobilized on the surface of a quantum dot (QD); wherein when the sensor is excited by an energy source: (i) in the absence of specific interaction between the target entity and the aptamer probe, a baseline signal is emitted, and (ii) in the presence of specific interaction between the target entity and the aptamer probe, a detection signal is emitted, wherein the baseline signal is weaker than the detection signal, whereby the presence of the target entity is detected. In the sandwich hybrid, preferably, the "tagged-FP-oligonucleotide" and the quencher-labeled-oligonucleotide are hybridized to opposite sides of the aptamer probe.

The aptamer probe comprises an aptamer and an attached tail sequence, wherein the tail sequence comprises two separate parts designated as "$1^{st}$ part of tail" and "$2^{nd}$ part of tail," wherein a portion of the quencher-labeled-oligonucleotide is hybridized to the "$1^{st}$ part of tail," and wherein the tagged-FP-oligonucleotide, or a portion thereof, is hybridized to the "$2^{nd}$ part of tail." The aptamer probe comprises a spacer nucleotide sequence between the "$1^{st}$ part of tail" and the "$2^{nd}$ part of tail." A portion of the "quencher-oligonucleotide" is hybridized to the "$1^{st}$ part of tail," and a portion of the quencher-labeled-oligonucleotide is hybridized to the aptamer, wherein the quencher-labeled-oligonucleotide disassociates from the sensor when the aptamer attaches to the target entity. Preferably, about 50% of quencher-labeled-oligonucleotide is hybridized to the "$1^{st}$ part of tail" and about 50% of the quencher-labeled-oligonucleotide is hybridized to the aptamer. The tagged-FP-oligonucleotide is immobilized on the surface of a QD by binding of a tag on the tagged-FP-oligonucleotide, wherein the distance between the fluorophore and the QD allows FRET.

In one embodiment, the invention is a method of determining if a target entity is present in a sample comprising: (a) contacting the sample with a signal-off-quantum-dot-based sensor; (b) contacting the sample with a quantum dot wherein the quantum dot is a FRET pair of the fluorophore; (c) exciting the signal-off-quantum-dot-based sensor with an energy source; and (d) determining the strength of emitted signal, thereby determining whether the target entity is present in the sample.

In another embodiment, the invention is a method of determining if a target molecule is present in a sample comprising: (a) contacting the sample with a signal-on-quantum-dot-based sensor; (b) contacting the sample with a quantum dot wherein the quantum dot is a FRET pair of the fluorophore; (c) exciting the signal-on-quantum-dot-based sensor with an energy source; and (d) determining the strength of emitted signal, thereby determining whether the target entity is present in the sample.

In comparison with prior art aptamer sensors, the sensors of the present invention have the significant advantages of simple sample preparation, high sensitivity and extremely low sample consumption.

DETAILED DESCRIPTION OF THE INVENTION

The present invention includes quantum-dot (QD)-based aptameric nanosensors, and methods of sensitively detecting target biological and chemical species.

Signal-OFF-quantum-dot-based Sensor

In one embodiment, the present invention is a signal-off-quantum-dot-based sensor for detecting the presence of a target entity. The signal-off-quantum-dot-based sensor comprises an aptamer probe having a nucleotide sequence which specifically interacts with the target. The aptamer probe is sandwiched between (a) an oligonucleotide which is labeled with a fluorophore (hereinafter "FP-oligonucleotide"); and (b) a "tagged-oligonucleotide" to form a sandwich hybrid. The tag allows the "tagged-oligonucleotide" to be immobilized on the surface of a quantum dot (QD).

Figure 7:
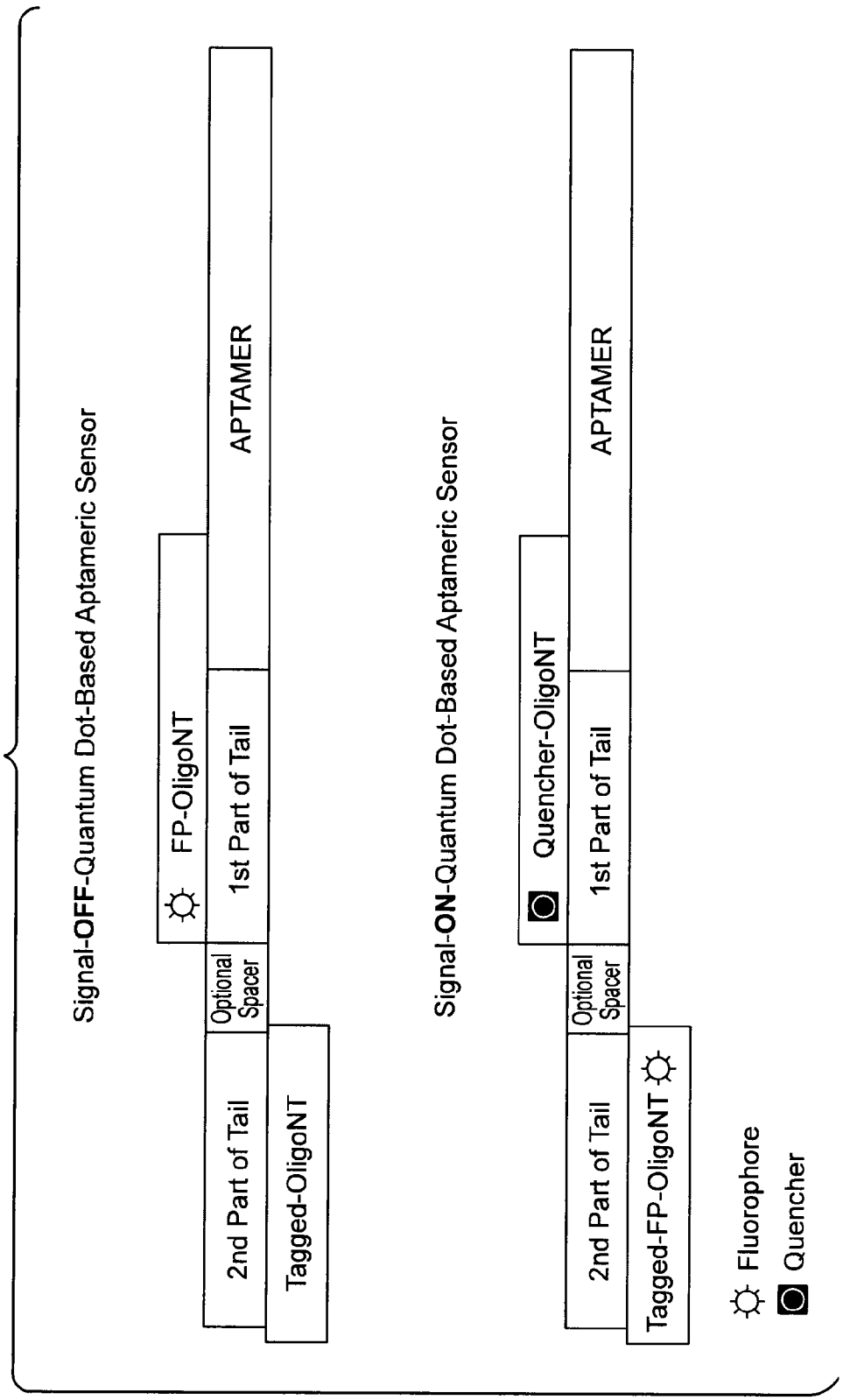
FIG. 7. Graphical depiction of a signal-off-QD-based aptameric sensor, and a signal-on-QD-based aptameric sensor.

The aptamer probe comprises an aptamer and an attached "tail sequence." The aptamer is the part of the aptamer probe that specifically interacts with the target. The "tail sequence" hybridizes with the other oligonucleotides of the sensor. Part of the "tail sequence" is hybridized to a portion of the "FP-oligonucleotide," designated herein as the "$1^{st}$ part of tail." Part of the "tail sequence" is hybridized to the "tagged-oligonucleotide" (or a portion thereof), designated herein as the "$2^{nd}$ part of tail." See FIG. 7.

A portion of the "FP-oligonucleotide" is hybridized to a portion of the aptamer; and a portion of the "FP-oligonucleotide" is hybridized to the "$1^{st}$ part of tail." The "FP-oligonucleotide" is hybridized in such a manner that it disassociates from the sensor when the aptamer attaches to a target. The "FP-oligonucleotide" is hybridized to the aptamer without interfering with the detection function of the aptamer. Preferably, the "FP-oligonucleotide" does not hybridize to the region of the aptamer that specifically binds/detects the target.

Typically, about 20% to about 50% of the "FP-oligonucleotide" is hybridized to the aptamer; and about 50% to about 80% is hybridized to the "$1^{st}$ part of tail"; or about 20% to about 50% of the "FP-oligonucleotide" is hybridized to the "$1^{st}$ part of tail" and about 50% to about 80% is hybridized to the aptamer. Preferably, about 50% of the "FP-oligonucleotide" is hybridized to the aptamer and about 50% is hybridized to the "$1^{st}$ part of tail." The greater the percentage of the "FP-oligonucleotide" hybridized to the aptamer vis-à-vis the "$1^{st}$ part of tail," the greater is the sensitivity of the sensor.

The sensitivity of the sensor can also be adjusted by varying the sequence of the "FP-oligonucleotide." Hybridization mismatches between the "FP-oligonucleotide" and the "$1^{st}$ part of tail" and/or the aptamer decreases the sensitivity of the sensor.

The "$2^{nd}$ part of tail" is hybridized to the "tagged-oligonucleotide." The "$2^{nd}$ part of tail" can be contiguous with the "$1^{st}$ part of the tail." Alternatively, the tail sequence can comprises about one to about five nucleotides between the "$1^{st}$ part of tail" and the "$2^{nd}$ part of tail," designated herein as a "spacer." The "$2^{nd}$ part of tail" can extend to the end of the "tagged-oligonucleotide," or can be a few nucleotides short of the end of the "tagged-oligonucleotide" (typically about five or less nucleotides short).

The signal-off-quantum-dot-based sensor comprises a QD attached to one or more of the sandwich hybrids. The QD is attached to the sandwich hybrid(s) by attaching to the end of the tagged-oligonucleotide via the tag. The number of sandwich hybrids that can be attached is limited by steric hindrance effects. For example, typically about eighteen sandwich hybrids are attached to a 605QD in the signal-off-quantum-dot-based sensor.

The QD and the fluorophore of the signal-off-QD-based-sensor constitute a Forster Resonance Energy Transfer pair (i.e., a "FRET" pair). (Selvin, P. R., "Fluorescence Resonance Energy Transfer," Methods in Enzymology 246: 300-335 (1995).) FRET pairs rely on energy transfer for signal generation. The mechanism of FRET-pair interaction requires that the absorption spectrum of one of the pair to overlap the emission spectrum of the other of the pair. The efficiency of FRET interaction is linearly proportional to that overlap.

The fluorophore is attached anywhere on the "FP-oligonucleotide" that would allow FRET between the fluorophore and the quantum dot. Preferably, the fluorophore is attached to the end of the "FP-oligonucleotide" which is hybridized to the "$1^{st}$ part of tail" so to avoid any interference with the detection function of the sensor.

It is critical that the distance between the fluorophore and the QD be such to allow for a FRET between the QD and the fluorophore. Thus, the length of the "$2^{nd}$ part of tail"; any "spacer"; and any part of the "tagged-oligonucleotide" that extends pass the "$2^{nd}$ part of tail" be a length which would allow a FRET between the QD and the fluorophore. The distance depends upon the particular fluorophore-QD pair used, as would be known by a skilled artisan. Typically, such length is about 10 nucleotides.

To use the signal-off-QD-based sensor for detection, it is excited with an energy source. The "baseline state" is when there is no specific interaction between a target and the aptamer. In the baseline state, the QD absorbs energy at a first wavelength and emits a second, longer wavelength; the fluorophore absorbs some or most of the emitted energy to the degree the fluorophore spectrum overlaps the emission spectrum; and the fluorophore then re-emits a fluorescence signal at a third, still longer wavelength. This fluorescence signal is the "baseline signal."

When the sensor comes into contact with a target, the aptamer specifically interacts with the target, and the "FP-oligonucleotide" is released, thereby eliminating the FRET between the QD and the fluorophore. This is the "detection state." Any signal observed at the detection state is the "detection signal." The baseline signal is greater than the detection signal by a certain threshold value, depending upon the particular QD and fluorophore used, as would be known by a skilled artisan. A difference in the baseline signal and the detection signal signify the presence of a target entity, and its amount.

Signal-ON-quantum-dot-based Sensor

In one embodiment, the present invention is a signal-on-quantum-dot-based sensor for detecting the presence of a target entity. The signal-on-quantum-dot-based sensor comprises an aptamer probe having a nucleotide sequence which specifically interacts with the target. The aptamer probe is sandwiched between (a) a tagged oligonucleotide which is labeled with a fluorophore (hereinafter "tagged-FP-oligonucleotide"), and (b) an oligonucleotide labeled with a quencher (hereinafter, "quencher-oligonucleotide") to form a sandwich hybrid. The tag allows the "tagged-FP-oligonucleotide" to be immobilized on the surface of a QD.

The aptamer probe comprises an aptamer and an attached "tail sequence." The aptamer is the part of the aptamer probe that specifically interacts with the target. The "tail sequence" hybridizes with the other oligonucleotides of the sensor. Part of the "tail sequence" is hybridized to a portion of the "quencher-oligonucleotide," designated herein as the "$1^{st}$ part of tail." Part of the "tail sequence" is hybridized to the "tagged-FP-oligonucleotide" (or a portion thereof), designated herein as the "$2^{nd}$ part of tail." See FIG. 7.

A portion of the "quencher-oligonucleotide" is hybridized to a portion of the aptamer; and a portion of the "quencher-oligonucleotide" is hybridized to the "$1^{st}$ part of tail." The "quencher-oligonucleotide" is hybridized in such a manner that it disassociates from the sensor when the aptamer attaches to a target. Preferably, the "quencher-oligonucleotide" does not hybridize to the region of the aptamer which specifically binds/detects the target.

Typically, about 20% to about 50% of the "quencher-oligonucleotide" is hybridized to the aptamer; and about 50% to about 80% is hybridized to the "$1^{st}$ part of tail"; or about 20% to about 50% of the "quencher-oligonucleotide" is hybridized to the "$1^{st}$ part of tail" and about 50% to about 80% is hybridized to the aptamer. Preferably, about 50% of the "quencher-oligonucleotide" is hybridized to the aptamer and about 50% is hybridized to the "$1^{st}$ part of tail." The greater the percentage of the "quencher-oligonucleotide" hybridized to the aptamer vis-à-vis the "$1^{st}$ part of tail," the greater is the sensitivity of the sensor.

The sensitivity of the sensor can also be adjusted by varying the sequence of the "quencher-oligonucleotide." Hybridization mismatches between the "quencher-oligonucleotide" and the "$1^{st}$ part of tail" and/or the aptamer decreases the sensitivity of the sensor.

The "$2^{nd}$ part of tail" is hybridized to the "tagged-FP-oligonucleotide." The "$2^{nd}$ part of tail" can be contiguous with the "$1^{st}$ part of tail." Alternatively, the tail sequence can comprises about one to about five nucleotides between the "$1^{st}$ part of tail" and the "$2^{nd}$ part of tail," designated herein as a "spacer." The "$2^{nd}$ part of tail" can extend to the end of the "tagged-FP-oligonucleotide," or can be a few nucleotides short of the end of the "tagged-FP-oligonucleotide" (typically about five or less nucleotides short).

The signal-on-quantum-dot-based sensor comprises a QD attached to one or more sandwich hybrids. The QD is attached to the sandwich hybrid(s) by attaching to the end of the "tagged-FP-oligonucleotide" via the tag. The number of sandwich hybrids that can be attached is limited by steric hindrance effects. For example, typically about twelve sandwich hybrids are attached to a 605QD in the signal-on-quantum-dot-based sensor.

The quantum dot and the fluorophore constitute a "FRET" pair. The fluorophore and the quencher constitute a "FRET" pair.

The fluorophore is attached anywhere on the "tagged-FP-oligonucleotide" and the quencher is attached anywhere on the "quencher-oligonucleotide" that would allow FRET between them, and between the quantum dot. Preferably, the fluorophore and tag are at opposite ends of the "tagged-FP-oligonucleotide" so to avoid any interference with the detection properties of the sensor. Preferably, the quencher is attached to the end of the "quencher-oligonucleotide" which is more proximate to the "$2^{nd}$ part of tail."

It is critical that the distance between the fluorophore, quencher, and the QD be such to allow for a FRET between the fluorophore, quencher and QD. Thus, the length of the "$2^{nd}$ part of tail"; any "spacer"; and any part of the "tagged-FP-oligonucleotide" that extends pass the "$2^{nd}$ part of tail" be a length which would allow the FRET. The distance depends upon the particular fluorophore, quencher and QD used, as would be known by a skilled artisan. Typically, such length is about 10 nucleotides.

To use the signal-on-QD-based sensor for detection, it is excited by an energy source. The "baseline state" is when there is no specific interaction between a target and the aptamer. In the baseline state, the QD absorbs energy at a first wavelength and emits a second, longer wavelength; the fluorophore absorbs the energy at a first wavelength and emits a second, longer wavelength; the quencher absorbs some or most of the emitted energy to the degree the quencher's spectrum overlaps the emission spectrum; and the quencher then releases the energy as heat. A weak signal may be observed, referred to as the "baseline signal."

When the sensor comes into contact with a target, the aptamer specifically interacts with the target, and the "quencher-oligonucleotide" is released, and a fluorescence signal is emitted, referred to as a "detection signal." The detection signal is greater than the baseline fluorescence signal by a certain threshold value, depending upon the particular QD, quencher and fluorophore used, as would be known by a skilled artisan. A difference in the baseline signal and the detection signal signify the presence of a target entity, and its amount.

Methods of Detecting Targets

The present invention includes methods to determine whether a target entity is present in a sample, and in what amount if any. In these methods, samples are prepared as would be known to a skilled artisan.

The methods can be used with both the signal-off-QD-based sensor and the signal-on-QD-based sensor. A sensor is selected with an aptamer to detect a particular target entity. A "baseline signal" of the sensor is determined (or obtained from an outside source). The "baseline signal" is the signal emitted by the sensor before contact with a sample. The "baseline signal" can be determined by exciting the sensor with an energy source. The energy source is preferably a laser, more preferably an argon laser.

For the signal-off-QD-based sensor, since the FRET pair is within a Förster distance, the "baseline signal" is at a maximum level.

For the signal-on-QD-based sensor, since the fluorescence is quenched, the "baseline signal" is at a minimum level.

A calibration is used. The calibration is determined (or obtained from an outside source). A calibration can be determined in the following manner. Samples with different known amounts of the particular target entity are provided, i.e., "known samples." The more samples of different amounts provided, the more precise will be the determination of the amount in the unknown sample. Sandwich hybrids of the sensors are placed into these known samples. Sandwich hybrids are the sensors without the QD. The sensors are used without the QD because the QD may interfere with the detection function of the aptamer. Then the QDs are introduced into the known samples and excited by an energy source.

For the signal-off-QD-based sensor, the greater the amount of the target entity in a known sample, the less fluorescence is emitted by the fluorophore. A curve can be produced to show how the fluorescence signal decreases with increasing amounts of the target entity. That is, a consequent drop in a sample's fluorescence signal from the baseline signal indicates the presence of a target entity. The extent of the drop indicates the amount of the target entity in the sample.

For the signal-on-QD-based sensor, the greater the amount of the target entity in a known sample, the more fluorescence is emitted by the fluorophore. A curve can be produced to show how the fluorescence signal increases with increasing amounts of the target entity.

The unknown sample is also contacted with the sandwich hybrid. Then QDs are placed into the unknown sample, and the unknown sample is excited by the same energy source as was the known samples. The fluorescence signal observed is compared to the corresponding calibration(s) to determine whether the target entity is present in the unknown sample, and in what amount if any.

In another embodiment, the unknown sample is contacted with the sensor with the QD attached. The unknown sample is excited by an energy source. The fluorescence signal observed is compared to the baseline signal to determine whether the target entity is present in the unknown sample. This embodiment can also use a calibration with known samples, preferably wherein the sensor is placed in the known samples with the QD attached.

Aptamers

Aptamers are nucleic acid binding species generated by in vitro selection. Aptamers can be RNA, modified RNA, single-stranded DNA or double-stranded DNA, and have been selected to bind a myriad of targets. Targets include small molecules, nucleic acids, metal ions, proteins and entire organisms.

Aptamers to be used in the present invention can be obtained from databases as would be known by a skilled artisan. One well-known database is updated monthly and is publicly available at http://aptamer.icmb.utexas.edu/.

Typically, aptamers contain a region that specifically interacts with a target. The mechanisms of specific interaction can vary. Some examples of mechanisms of specific interaction include stacking interactions (in particular with protein targets), complementarity, electrostatic interactions, hydrogen binding, noncovalent chemical bonds, and combinations thereof. The length of a specifically interacting region depends upon the target to be detected. Typically, surrounding the specifically interacting region of the aptamer, on both sides, are regions which allow for hair pin hybridization loops to form when a target is detected in order to stabilize the specific interaction.

Some examples of targets include antibiotics, growth factors, metabolites, bacterial spores, viruses, hormones, microorganisms, pharmaceuticals and cancer cells. More specific examples of targets include thrombin, neomycin, inosine monophosphate dehydrogenase II, vascular endothelial growth factor, basic fibroblast growth factor, HIV-Tat protein, SARS coronavirus, anthrax, abrin, follicle stimulating hormone, leukemia cell, angiogenin, and cocaine.

Clinical applications or applications related to Homeland Security may require detection of any organism of interest. For example, not only human viruses (such as, for example, human immunodeficiency virus (HIV), hepatitis C virus (HCV), hepatitis B virus (HVB), small pox, Ebola, human papilloma virus (HPV), and flu viruses) but also viruses of agricultural importance, (such as, for example, viruses causing hoof and mouth disease), bacteria (including, for example, Anthrax, Staphylococcus, Streptococcus, and Borrelia), and infection-causing protozoa.

Other applications include the real time detection of toxicity markers, including the detection of specific stress proteins, and stress induced changes in expression and modification of DNA and RNA. In particular, the methods of the invention could be used to detect changes in gene expression, changes in gene regulation detectable via the induction of specific siRNAs, SNP, target DNAs secreted by specific tumor lines, etc.

The aptamer probes of the present invention comprise aptamers which specifically interact with the selected target entity, as would be known by a skilled artisan.

Fluorophores

Some examples of fluorophores that can be used in the present invention include a xanthene dye, a cyanine dye, a dansyl derivative, EDANS, coumarin, such as 3-phenyl-7-isocyanatocoumarin, Lucifer yellow, BODIPY, Cy3, Cy5, Cy7, Texas red, erythrosine, naphthylamine, Oregon green, ALEXA fluor dyes, acridines, such as 9-isothiocyanato-acridine and acridine orange, N-(p-(2-benzoxazolyl)phenyl)maleimide, benzoxadiazoles, stilbenes, and pyrenes.

The xanthene dye can be fluorescein or rhodamine. Preferably, the fluorescein is 5-carboxyfluorescein (5-FAM); 6-carboxyfluorescein (6-FAM); 2',4',1,4,-tetrachlorofluorescein (TET); 2',4',5',7',1,4-hexachlorofluorescein (HEX);

eosin; calcium green; fluorescein isothiocyanate (FITC); or NED. Preferably, the rhodamine dye is tetramethyl-6-carboxyrhodamine (TAMRA); tetrapropano-6-carboxyrhodamine (ROX); 2',7'dimethoxy-4',5'-dichloro-6-carboxyrhodamine (JOE) or tetramethylrhodamine (TMR). Many suitable forms of these compounds are commercially available with various substituents on their xanthene rings which can be used as the site for bonding or as the bonding functionality for attachment to an oligonucleotide.

The fluorophore can also be a naphthylamine compound. The naphthylamine compounds have an amino group in the alpha or beta position. Included among such naphthylamino compounds are 1-dimethylaminonaphthyl-5-sulfonate, 1-anilino-8-naphthalene sulfonate and 2-p-toluidinyl-6-naphthalene sulfonate.

The fluorophore can also be a combination fluorophore. Examples of a combination fluorophores are fluorescein-rhodamine dimers, described, for example, by Lee et al. (1997), Nucleic Acids Research 25:2816. Fluorophores may be chosen to absorb and emit in the visible spectrum or outside the visible spectrum, such as in the ultraviolet or infrared ranges.

Quenchers

Some examples of quenchers suitable for the present invention include Iowa Black, DABCYL, anthroquinone, nitrothiazole, nitroimidazole or malachite green. Variants of DABCYL, such as DABSYL, DABMI or methyl red, are also suitable.

Additionally, fluorophores can also be used as the quenchers. For example, fluorophores that do not fluoresce in the detection range when the probe is in the open conformation can quench fluorescence when in proximity with certain other fluorophores.

Quantum Dots

Quantum dots are semiconductor nanocrystals. Quantum dots (QDs) have broad excitation and size-tunable photoluminescence spectra with narrow emission bandwidth (full-width at half-maximum of ~25-40 nm), exceptional photochemical stability and relative high quantum yields.

Some examples of quantum dots that are suitable for the present invention include the transition metal chalcogenides. Examples of transition metal chalcogenide nanocrystal include zinc sulfide, zinc selenide, zinc telluride, cadmium sulfide, cadmium selenide, cadmium telluride, mercury sulfide, mercury selenide and mercury telluride. Further examples of quantum dots include gallium arsenide, indium gallium arsenide, indium phosphide, indium arsenide, germanium and silicon. Preferably, the quantum dots of the heterostructures are wurtzite cadmium selenide, cadmium sulfide, cadmium telluride, zinc selenide, and zinc sulfide.

Quantum dots exhibit strongly size-dependent optical and electrical properties. In particular, the band gap of these quantum dots increases with decreasing particle size. (Alivisatos, A. P. J. Phys. Chem. 100:13226-39 (1996).) For example, by varying the particle size of CdS, the band gap can be tuned between 2.5 and 4 eV. The size of quantum dots can be varied by methods known in the art.

Tags to Immobilize Oligonucleotides on the Surface of the QD

The "tagged-oligonucleotide" and the "tagged-FP-oligonucleotide" can be immobilized on the surface of the QD, as would be known by a skilled artisan. For example, binding pairs can be used. One member of the binding pair is placed on the QD, and the other member of the binding pair is placed on the oligonucleotide. The binding pairs do not interfere with the detection function of the sensors.

Examples of binding pairs suitable for the invention include receptors and their ligands; antibodies and their antigens (both protein and non-protein antigens); and protein affinity tags and moieties recognized by the tags. A preferred example of a binding pair is biotin-avidin. Preferably, the biotin is placed on the "tagged-oligonucleotide" and the "tagged-FP-oligonucleotide."

Affinity tags can be generated against the surfaces of metallic particles. Generation of such specifically-bindable-nanoparticle is known in the art. See Sarikaya et al., "Molecular Biomimetics: Nanotechnology through Biology," Nature Materials 2:577-585 (2003).

One Embodiment of the Invention

A signal-off single-quantum-dot-based detector or sensor for determining the presence of a target molecule comprising: a single-Quantum Dot (QD); an aptamer oligonucleotide probe having a nucleotide sequence which specifically interacts with the target molecule by sequence-dependent interaction; and said aptamer probe being sandwiched by a biotinylated oligonucleotide and a Cy5-labeled oligonucleotide to form a sandwich hybrid; and said aptamer sandwich hybrid then being immobilized on the surface of the QD through biotin-streptavidin binding to form a QD/aptamer/Cy5 complex; and when said complex is excited by a laser, in the absence of hybridization between the target molecule and said aptamer probe, strong Cy5 fluorescence signal being detected due to fluorescence resonance energy transfer (FRET) between the QD and Cy5 and, in the presence of hybridization between the target molecule and the aptamer probe, said FRET being absent and said Cy5 fluorescence signal being decreased and, said weak and strong Cy5 fluorescence signal giving distinguishable difference to determine presence or absence of the target molecule. The target molecule is one of the following: cocaine, small molecules, nucleic acids, metal ions and proteins. The QD is a 605QD and the laser is a 488-nm argon laser.

A signal-on single-quantum-dot-based detector or sensor for determining the presence of a target molecule comprising; a single-Quantum Dot (QD), an aptamer oligonucleotide probe having a nucleotide sequence which specifically interacts with the target molecule by sequence-dependent interaction; and said aptamer probe being sandwiched by a 5'-Cy5-labeled and 3'-biotinylated oligonucleotide and a quencher of Iowa Black RQ-labeled oligonucleotide to form a sandwich hybrid; and said aptamer sandwich hybrid then being immobilized on the surface of the QD through biotin-streptavidin binding to form a QD/aptamer/Cy5/Iowa Black RQ complex; and when said complex is excited by a laser, in the absence of hybridization between the target molecule and said aptamer probe, weak Cy5 fluorescence signal being detected as a result of the quenching effect of the Iowa Black RQ due to fluorescence resonance energy transfer (FRET) between Cy5 and Iowa Black RA and, in the presence of hybridization between the target molecule and said aptamer probe, said FRET being absent and said Cy5 fluorescence signal being strong and, said strong and weak Cy5 fluorescence signal giving distinguishable difference to detect presence or absence of the target molecule. The target molecule is one of the following: cocaine, small molecules, nucleic acids, metal ions and proteins. The QD is a 605QD and said laser is a 488-nm argon laser. The target molecule is one of the following: cocaine, small molecules, nucleic acids, metal ions and proteins.

EXAMPLES

By functionalizing the surface of a QD with aptamers which can recognize cocaine, and taking advantage of single-molecule detection and fluorescence resonance energy transfer (FRET) between 605QD and Cy5 and Iowa Black RQ, a single QD-based aptamer sensor is demonstrated that is capable of sensing the presence of cocaine through both signal-off and signal-on modes, with simple sample preparation, extremely high sensitivity and low sample consumption.

Signal-OFF Single-QD-based Aptameric Sensor

Figure 1:
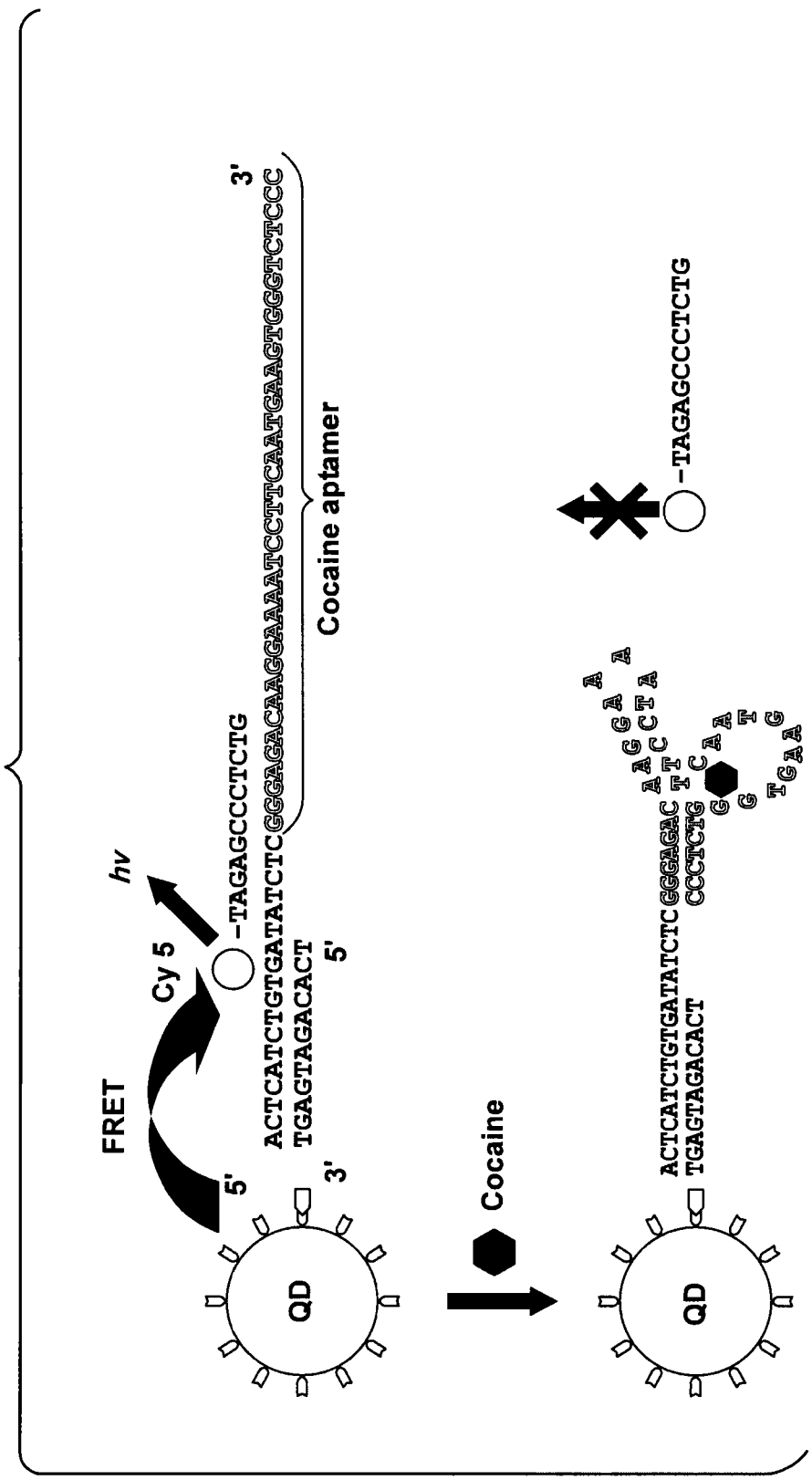
FIG. 1. Principle of signal-off single QD-based aptameric sensor for cocaine detection. In the absence of cocaine, Cy5 fluorescence was detected due to FRET between 605QD and Cy5. While the presence of cocaine led to the formation of a complex structure of a cocaine aptamer complex, and the subsequent abolishment of FRET between 605QD and Cy5, the decrease of Cy5 signal signified the presence of cocaine.

In one embodiment of the present invention, a signal-off single-QD-based aptamer sensor is provided. An example of a preferred design of a signal-off single-QD-based aptamer sensor is shown in FIG. 1. The cocaine aptamer was sandwiched by a biotinylated oligonucleotide and a Cy5-labeled oligonucleotide; this sandwich hybrid was then assembled on the surface of a 605QD through biotin-streptavidin binding to form the 605QD/aptamer/Cy5 complex.

Figure 2:
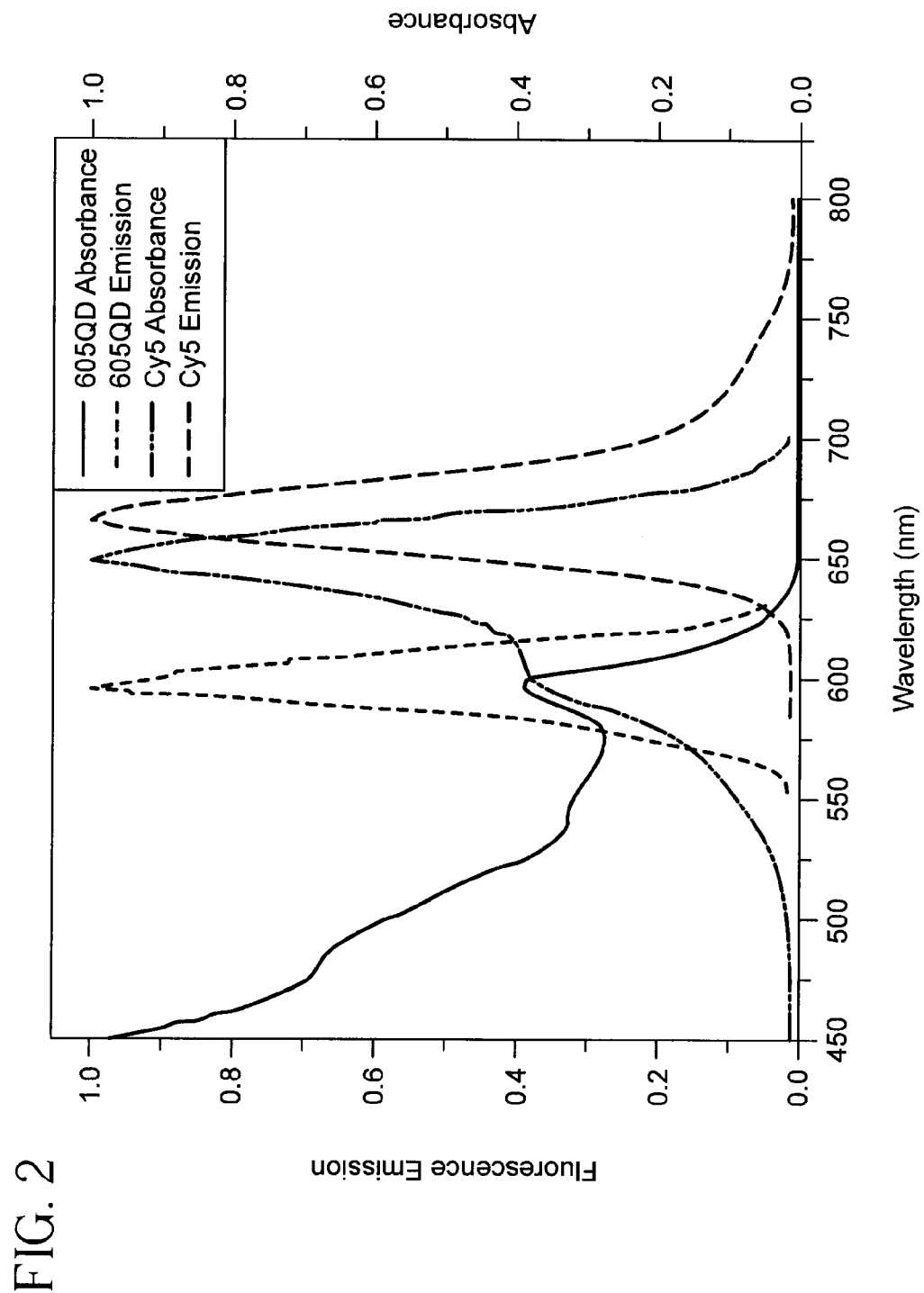
FIG. 2. Normalized absorption and emission spectra of the 605QD and Cy5. Blue line, absorption spectrum of the 605QD; magenta line, emission spectrum of the 605QD; green line, absorption spectrum of Cy5; red line, emission spectrum of Cy5.

In this complex, the 605QD served as a FRET donor to transfer energy to Cy5. The selection of 605QD as an energy donor and Cy5 as an acceptor was based on the following reasons: (1) There is no cross-talk between the emission spectra of 605QD and that of Cy5; (2) There is no direct excitation of Cy5 at the wavelength of 488 nm (FIG. 2); (3) 605QD has a high quantum yield (~0.6); (4) Cy5 has a high extinction coefficient (~250,000 $M^{-1}cm^{-}$); The Förster distance ($R_0$) is 69.4 Å for the 605QD/Cy5 FRET pair.

In addition, a single 605QD can efficiently couple to multiple Cy5-labeled sandwich hybrids. Therefore, 605QD also served as a nanoscaffold to amplify the FRET signals. The nanoscaffold function of 605QD created a high local concentration of aptamer, which thermodynamically favored the formation of more aptamer-cocaine complexes. When this complex was excited by a 488-nm argon laser, Cy5 fluorescence was detected due to FRET between 605QD and Cy5. The presence of cocaine led to the formation of complex structure of a cocaine-aptamer complex, which made Cy5-labeled oligonucleotide dissociate from aptamer and 605QD; the subsequent decrease of Cy5 signal due to the absence of FRET between 605QD and Cy5 signified the presence of cocaine (FIG. 1).

Figure 3:
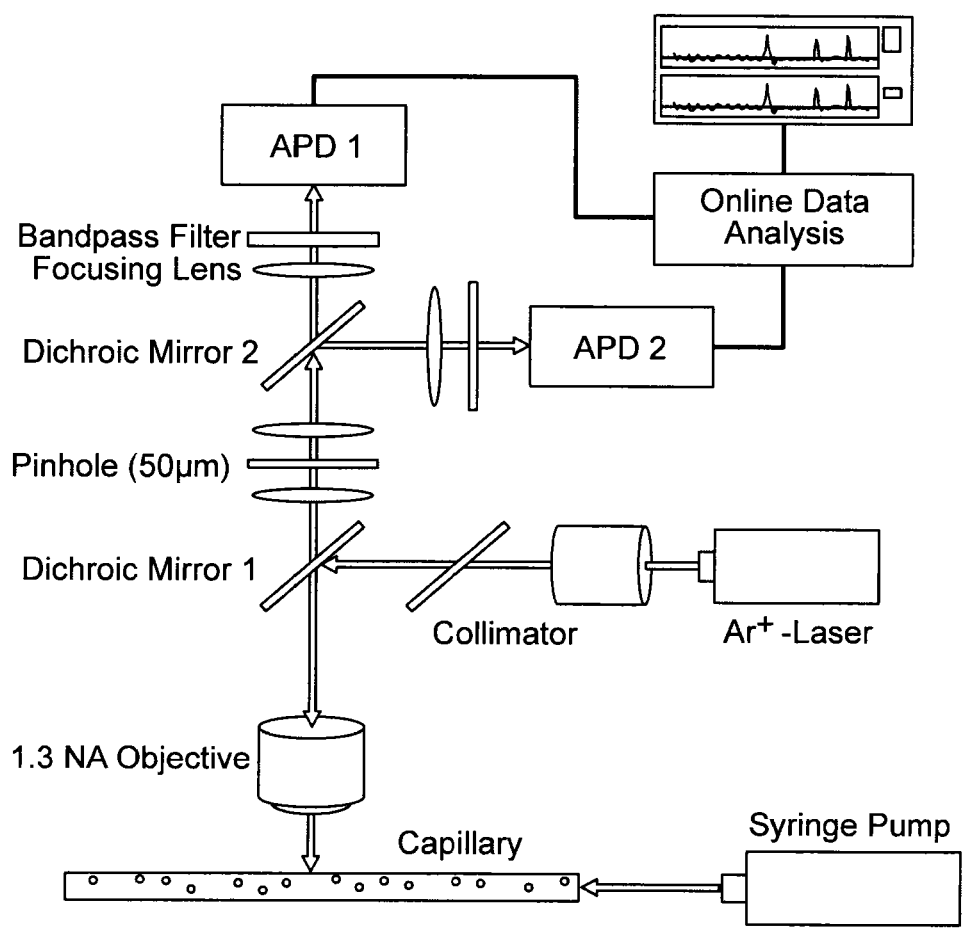
FIG. 3. Schematic view of the experimental apparatus used for simultaneous detection of the photons emitted from the single 605QD and Cy5. Photons emitted from the 605QD and Cy5 were separated by dichroic mirrors and detected by two avalanche photodiodes (APDs), respectively.

The schematic for the experimental setup is shown in FIG. 3. An argon laser was used as the excitation light source. The 488 nm beam was focused on the center of a 50 μm ID capillary by an oil immersion 100×/1.30 NA objective; the sample was moved through a laser-focused detection volume at a flow rate of 1.0 μL $min^{-1}$ by the pressure-driven flow from a syringe pump. Photons emitted from the 605QD and Cy5 were separated by dichroic mirrors and detected by two avalanche photodiodes (APDs), respectively. The performance of single-QD-based FRET in a microfluidic flow has another significant advantage of improved FRET efficiency, which might even break the FRET limit.

Detection of Cocaine with Signal-off Single QD-based Aptameric Sensor.

Figure 4A:
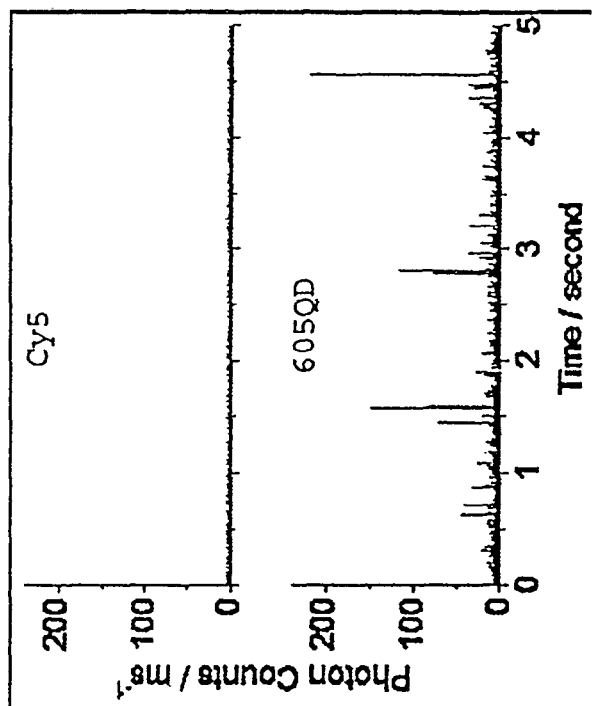
FIG. 4. Detection of cocaine with signal-off single QD-based aptameric sensor. (A) Representative traces of fluorescence bursts from 605QD/aptamer/Cy5 complexes. The top panel shows the Cy5 fluorescence signals; the bottom panel shows the 605QD fluorescence signals. (B)Representative traces of fluorescence bursts from 605QD/aptamer complexes without Cy5 binding. The top panel shows the Cy5 fluorescence signals; the bottom panel shows the 605QD fluorescence signals. (C) Variance of Cy5 burst counts as a function of increasing Cy5-to-605QD ratio in 605QD/aptamer/Cy5 complexes. (D) Variance of Cy5 burst counts as a function of increasing cocaine concentration. The Cy5-to-605QD ratio is 18:1. Error bars show the standard deviation of three experiments.

FIG. 4A shows the representative trace of fluorescence bursts from 605QD/aptamer/Cy5 complexes. Distinct Cy5 bursts are observed with corresponding 605QD bursts, indicating the FRET between 605QD and Cy5.

Figure 4B:
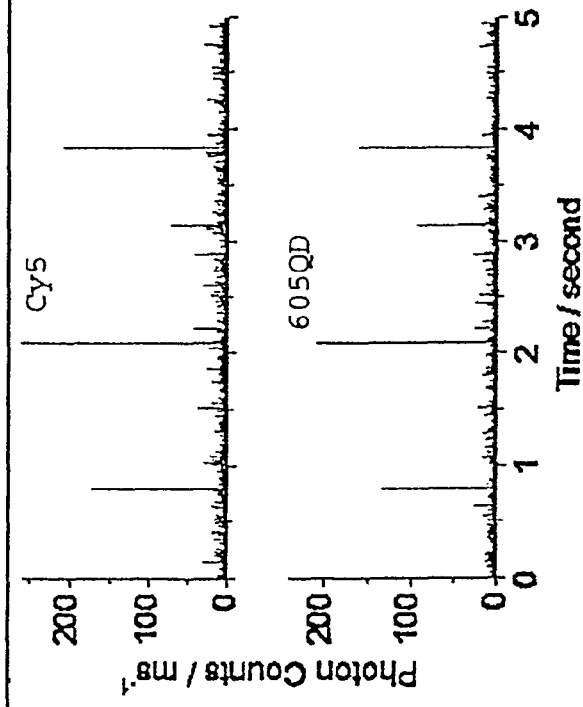
Figure 4D:
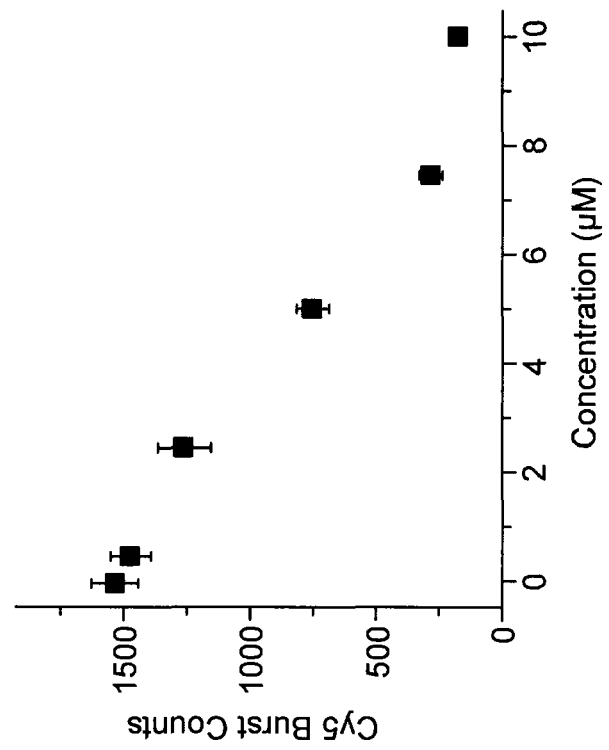
Figure 4C:
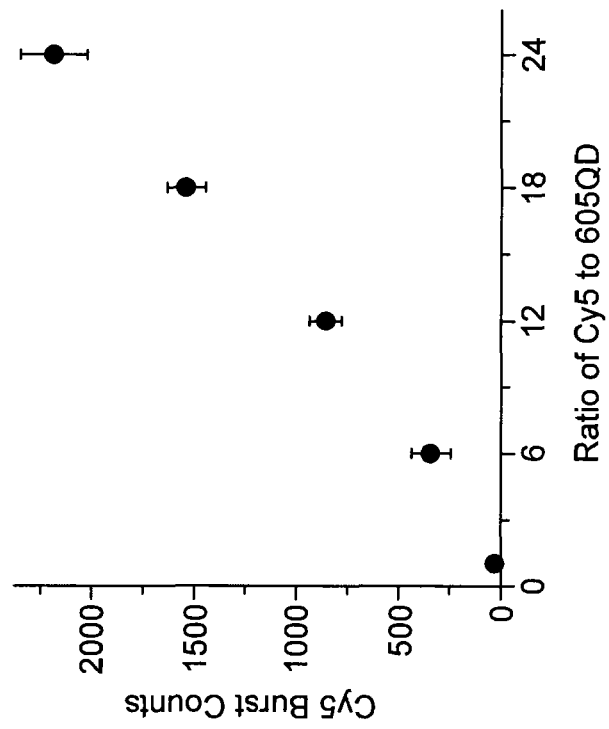

FIG. 4B shows the representative trace of fluorescence bursts from 605QD/aptamer complex without Cy5 binding. No Cy5 bursts are observed due to the absence of FRET between 605QD and Cy5. Moreover, in the 605QD/aptamer/Cy5 complexes, the Cy5 burst counts increased linearly as a function of increasing Cy5-to-605QD ratio (FIG. 4C); even one copy difference of Cy5-labeled oligonucleotide bound to 605QD can be distinguished, suggesting the high sensitivity of this single-QD-based aptamer sensor. In the presence of cocaine, its binding to the aptamer triggered the release of Cy5-labeled oligonucleotide from 605QD and consequently the abolishment of FRET between 605QD and Cy5. As a result, the Cy5 burst counts decreased as a function of increasing cocaine (FIG. 4D). The detection limit can reach 0.5 μM. This is at least two orders of magnitude improvement over the conventional nanoparticle-based colorimetric method, where large amount of nanoparticles and relatively high concentration of cocaine are required to produce observable aggregation or disassembly of nanoparticles.

Even though cocaine-aptamer complexes were unstable at low concentration in single-molecule measurement, this did not reduce the final detection sensitivity of current single-QD-based aptamer sensor, because the dissociated Cy5-labeled oligonucleotide can not reassemble to the 605QD in the single-molecule measurement, and only the Cy5 bound to 605QD contributed to the FRET signals.

Compared to established aptamer sensors, one major advantage of this single-QD-based aptameric sensor lies in its ability to measure extremely low concentration molecules down to a single particle with near-zero background noise (FIG. 4A,B), which significantly improves the detection sensitivity of this QD-based aptameric sensor.

In theory, as few as several molecules of cocaine can induce observable FRET changes in one single-QD, which can be sensitively detected by single QD-based aptamer sensor.

Signal-ON Single-QD-based Aptamer Sensor

In another embodiment of the present invention, a signal-on single-QD-based aptamer sensor is provided. A preferred example of such a sensor is shown in FIG. 5.

A cocaine aptamer was sandwiched by a 5'-Cy5-labeled and 3'-biotinylated oligonucleotide and a quencher of Iowa Black RQ-labeled oligonucleotide; this sandwich hybrid was then assembled on a 605QD through biotin-streptavidin binding to form 605QD/aptamer/Cy 5/Iowa Black RQ complex.

Even though FRET could potentially occur between 605QD and Cy5 in this 605QD/apatmer/Cy5/Iowa Black RQ complex when it was excited by a 488-nm argon laser, the Cy5 fluorescence is quenched by the nearby Iowa Black RQ due to FRET between Cy5 and Iowa Black RQ; therefore, Cy5 was in the fluorescence 'OFF' state.

Figure 5:
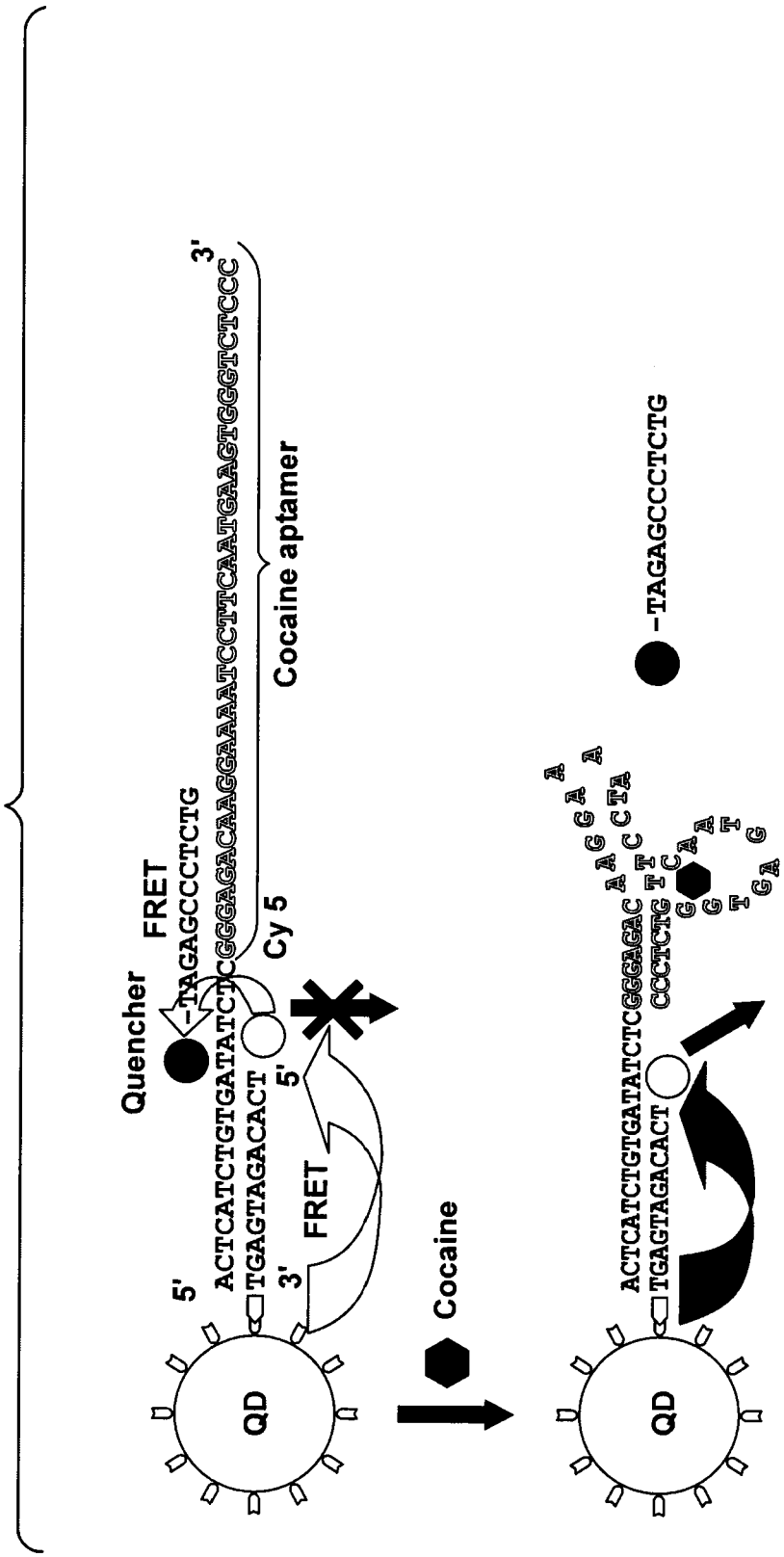
FIG. 5. Principle of signal-on single QD-based aptameric sensor for cocaine detection. In the absence of cocaine, Cy5 was in the fluorescence "OFF" state due to FRET between Cy5 and Iowa Black RQ. While the presence of cocaine led to the formation of a complex structure of a cocaine-aptamer complex, and the subsequent abolishment of FRET between Cy5 and Iowa Black RQ, the Cy5 fluorescence was activated to the "ON" state.

The addition of cocaine induced the release of the Iowa Black RQ-labeled oligonucleotide from the aptamer and the 605QD; subsequently the Cy5 fluorescence was activated to 'ON' state (FIG. 5). In comparison with the signal-off sensor, the signal-on sensor is much more straightforward.

Detection of Cocaine with Signal-on Single QD-based Aptameric Sensor.

Figure 6A:
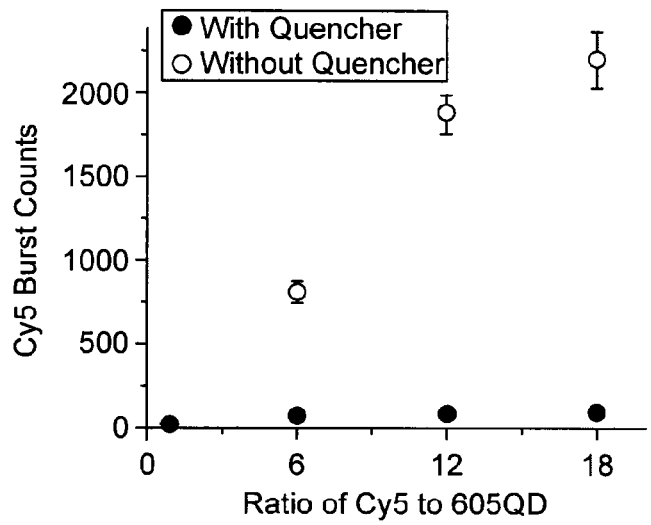
FIG. 6. Detection of cocaine with signal-on single QD-based aptameric sensor. (A) Variance of Cy5 burst counts as a function of increasing Cy5-to-605QD ratio in 605QD/aptamer/Cy5 complexes (o) and 605QD/apatmer/Cy5/Iowa Black RQ complexes (•). (B) Variance of 605QD burst counts as a function of increasing Cy5-to-605QD ratio in 605QD/aptamer/Cy5 complexes (o) and 605QD/apatmer/Cy5/Iowa Black RQ complexes (•). (C) Variance of Cy5 burst counts as a function of increasing cocaine concentration. The Cy5-to-605QD ratio is 12:1. Error bars show the standard deviation of three experiments.
Figure 6B:
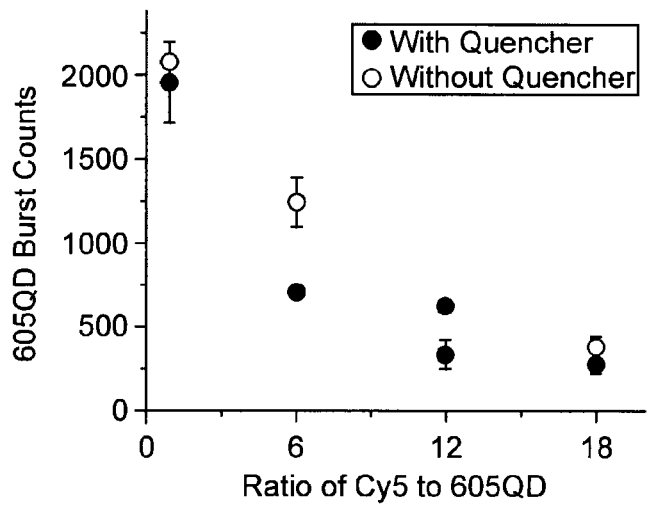

FIG. 6A shows the comparison of Cy5 burst counts from the 605QD/aptamer/Cy5 complex and the 605QD/aptamer/Cy5/Iowa Black RQ complex. Without the quencher of Iowa Black RQ, the Cy5 burst counts increased as a function of the increasing Cy5-to-605QD ratio. In contrast, no change in Cy5 burst counts was observed in the presence of Iowa Black RQ despite the increasing Cy5-to-605QD ratio, suggesting Iowa Black RQ completely quenched the Cy5. It was worth noting that Iowa Black RQ not only quenched Cy5, but also quenched 605QD to some extent, which was confirmed by the decrease of 605QD burst counts. (FIG. 6B).

In addition, the selection of the Cy5-to-605QD ratio is very important for the detection of cocaine with the signal-on single-QD-based aptameric sensor because the Cy5-to-605QD ratio might significantly influence the dynamic range of cocaine detection. To obtain the best dynamic range, the Cy5-to-605QD ratio of 12:1 was used in the experiments.

In the presence of cocaine, its binding to the aptamer triggered the release of Iowa Black RQ-labeled oligonucleotide from the aptamer and 605QD, and consequently the Cy5 fluorescence became detectable; the increase of Cy5 signal signified the presence of cocaine.

Figure 6C:
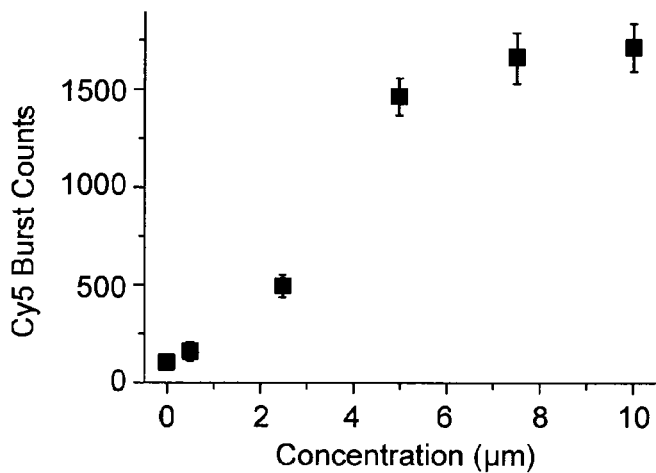

As shown in FIG. 6C, the Cy5 burst counts increased as a function of increasing cocaine concentration. The detection limit of the signal-on single-QD aptameric sensor was of the same order of magnitude as that of the signal-off sensor.

The main challenge with an aptameric sensor for cocaine is that the detection sensitivity is limited by its relatively low association constant. The reported best detection limits are 10 µM of cocaine for electrochemical method, 5.0 µM for an autonomous aptamer-based enzymatic assay, 10 µM for bulk fluorescence assay, and 0.5 µM for aptamer-based colorimetric probes. The detection limit of single-QD-based aptameric sensor is comparable with those reported aptameric sensors, but does not involve the complicated sample preparation and large sample consumption.

Most analytical laboratories currently utilize mass-spectral analysis to detect cocaine which involves the use of stable isotopes as internal standards or the available high-resolution mass spectra as a reference, long-time sample preparation, and application of expensive mass-spectral instruments. In contrast, this single-QD-based aptameric sensor takes advantage of a simple "mix and detection" assay, and has potential to be applied for rapid point-of-care testing and field detection of cocaine.

Methods and Materials

Sample preparation

In the instant example, the following was designed: a biotinylated oligonucleotide (5'-TCA CAG ATG AGT-Biotin-3'), Cy5-labeled oligonucleotide (5'-GTC TCC CGA GAT-Cy5-3'), a cocaine aptamer (5'-ACT CAT CTG TGA TAT CTC GGG AGA CAA GGA AAA TCC TTC AAT GAA GTG GGT CTC CC-3'), a 5'-Cy5-labeled and 3'-biotinylated oligonucleotide (5'-Cy5-TCA CAG ATG AGT-Biotin-3'), and a 3'-Iowa Black RQ-labeled oligonucleotide (5'-GTC TCC CGA GAT-Iowa Black RQ-3') as models for the detection of cocaine. All oligonucleotides had been purified by high-performance liquid chromatography when purchased from Integrated DNA Technology Inc. (Coralville, Iowa). (The following cocaine aptamer can also be used (5'-ACT CAT CTG TGA TAT CTC GGG AGA CAA GGA TAA ATC CTT CAA TGA AGT GGG TCT CCC-3').)

For the signal-off single-QD-based aptamer sensor, the aptamer sandwich hybrids were formed by a biotinylated oligonucleotide, Cy5-labeled oligonucleotide and an aptamer in 100 mM NaCl, 25 mM Tris acetate, 1 mM MgCl$_2$, pH 8.2 from 60° C. to 4° C.

For the signal-on single-QD-based aptamer sensor, the aptamer sandwich hybrids were formed by a 5'-Cy5-labeled and 3'-biotinylated oligonucleotide, 3'-Iowa Black RQ-labeled oligonucleotide and aptamer in 100 mM NaCl, 25 mM Tris acetate, 1 mM MgCl$_2$, pH 8.2 from 60° C. to 4° C.

For the detection of cocaine, the aptamer sandwich hybrids were incubated with cocaine (Sigma-Aldrich) at 30° C., followed by adding streptavidin-functionalized 605QDs (Invitrogen Corp., Carlsbad, Calif. and/or Quantum Dot Corp., Hayward, Calif.) to capture the aptamer hybrids through biotin-streptavidin binding. Finally the solution was subjected to single-molecule detection at the QD concentration of $2.5 \times 10^{-11}$ M.

Experimental Setup for Single-Molecule Detection

An argon laser was used as the excitation light source for 605QD. The 488-nm beam was collimated, reflected by a dichroic mirror (Z488RDC, Chroma Technology Corp, Rockingham, Vt.), and then focused by an oil immersion 100×/1.30 NA objective lens (Olympus America, Inc., Melville, N.Y.) on the center of a 100-µm ID square capillary (and/or a 50-µm ID capillary); the sample was moved through a laser-focused detection volume by the pressure-driven flow from a syringe pump (Harvard Apparatus, Holliston, Mass.). Photons emitted from 605QD and Cy 5 were collected by the same objective, passed through the first dichroic mirror, followed by a 50 µm pinhole (Melles Griot Co, Irvine, Calif.), and then separated by second dichroic mirror (645DCLP, Chroma Technology Corp, Rockingham, Vt.). After separation, the signal emitted from Cy 5 was filtered by a band-pass filter (D680/30M, Chroma Technology Corp, Rockingham, Vt.) and detected by an avalanche photodiode (Model SPCM-AQR-13, EG&G Canada, Vaudreuil, PQ, Canada) in the acceptor channel. At the same time, photons emitted from 605QD were filtered by a band-pass Filter (D605/20M, Chroma Technology Corp, Rockingham, Vt.) and detected by an avalanche photodiode in the donor channel. A program written with Labview (National Instruments, Austin, Tex.) and a digital counter (National Instruments, Austin, Tex.) were used to perform data acquisition and on-line data analysis. Fluorescent signals from both donor and acceptor channels were integrated in 1-ms interval for a total running time of 100 s for each experiment. In single-molecule detection, a threshold was used to distinguish single-molecule fluorescence signal from random fluctuation in the background. The threshold value is determined by evaluating data from control sample. In this study, a threshold of 10 photon counts ms$^{-1}$ was set for Cy5, and a threshold of 10 photon counts ms$^{-1}$ was set for 605QD.

Incorporation Of Sequence Listing

Incorporated herein by reference in its entirety is the Sequence Listing for the application. The Sequence Listing is disclosed on a computer-readable ASCII text file entitled, "SeqList2_1038_51PCTUS.txt", created on Jul. 29, 2011. The sequence.txt file is 1.46 KB in size.

The invention claimed is:

1. A signal-off-quantum-dot-based sensor for detecting the presence of a target entity comprising:
    an aptamer probe having a nucleotide sequence which specifically interacts with the target entity, wherein the aptamer probe is sandwiched between (a) a tagged-oligonucleotide which is capable of being immobilized on the surface of a quantum dot (QD), and (b) an oligonucleotide labeled with a fluorophore, designated as "FP-oligonucleotide," wherein when the sensor is excited by an energy source:
        (i) in the absence of specific interaction between the target entity and the aptamer probe, a baseline signal is emitted, and
        (ii) in the presence of specific interaction between the target entity and the aptamer probe, a detection signal is emitted,
    wherein if the baseline signal is a stronger fluorescence signal than the detection signal, the presence of the target entity is detected.

2. The sensor of claim 1, wherein the target entity is a small molecule, a nucleic acid, a metal ion, a protein, or a microorganism.

3. The sensor of claim 1, wherein the aptamer probe comprises an aptamer and an attached tail sequence, wherein the tail sequence comprises two separate parts designated as "1$^{st}$ part of tail" and "2$^{nd}$ part of tail," wherein a portion of the "FP-oligonucleotide" is hybridized to the "1$^{st}$ part of tail," and wherein the tagged-oligonucleotide, or a portion thereof, is hybridized to the "2$^{nd}$ part of tail".

4. The sensor of claim 3, wherein the aptamer probe comprises a spacer nucleotide sequence between the "1$^{st}$ part of tail" and the "2$^{nd}$ part of tail".

5. The sensor of claim 3, wherein a portion of the "FP-oligonucleotide" is hybridized to the "1$^{st}$ part of tail," and a portion of the "FP-oligonucleotide" is hybridized to the aptamer, wherein the "FP-oligonucleotide" disassociates from the sensor when the aptamer attaches to the target entity.

6. The sensor of claim 5, wherein about 50% of "FP-oligonucleotide" is hybridized to the "1$^{st}$ part of tail"; and about 50% of the "FP-oligonucleotide" is hybridized to the aptamer.

7. The sensor of claim 1, wherein the tagged-oligonucleotide is immobilized on the surface of a QD by binding of a tag on the tagged-oligonucleotide, wherein the distance between the fluorophore and the QD allows FRET.

8. A signal-on-quantum-dot-based sensor for detecting the presence of a target entity comprising:
   an aptamer probe having a nucleotide sequence which specifically interacts with the target molecule, wherein the aptamer probe is sandwiched between (a) a quencher-labeled oligonucleotide; and (b) an oligonucleotide which is tagged and labeled with a fluorophore, designated as "tagged-FP-oligonucleotide," wherein the "tagged-FP-oligonucleotide" is capable of being immobilized on the surface of a quantum dot (QD);
   wherein when the sensor is excited by an energy source:
      in the absence of specific interaction between the target entity and the aptamer probe, a baseline signal is emitted, and
      (ii) in the presence of specific interaction between the target entity and the aptamer probe, a detection signal is emitted,
   wherein if the baseline signal is a weaker fluorescence signal than the detection signal, the presence of the target entity is detected.

9. The sensor of claim 8, wherein the target entity is a small molecule, a nucleic acid, a metal ion, a protein, or a microorganism.

10. The sensor of claim 8, wherein the aptamer probe comprises an aptamer and an attached tail sequence, wherein the tail sequence comprises two separate parts designated as "1$^{st}$ part of tail" and "2$^{nd}$ part of tail," wherein a portion of the quencher-labeled-oligonucleotide is hybridized to the "1$^{st}$ part of tail," and wherein the tagged-FP-oligonucleotide, or a portion thereof, is hybridized to the "2$^{nd}$ part of tail".

11. The sensor of claim 10, wherein the aptamer probe comprises a spacer nucleotide sequence between the "1$^{st}$ part of tail" and the "2$^{nd}$ part of tail".

12. The sensor of claim 10, wherein a portion of the "quencher-oligonucleotide" is hybridized to the "1$^{st}$ part of tail," and a portion of the quencher-labeled-oligonucleotide is hybridized to the aptamer, wherein the quencher-labeled-oligonucleotide disassociates from the sensor when the aptamer attaches to the target entity.

13. The sensor of claim 12, wherein about 50% of quencher-labeled-oligonucleotide is hybridized to the "1$^{st}$ part of tail" and about 50% of the quencher-labeled-oligonucleotide is hybridized to the aptamer.

14. The sensor of claim 8, wherein the tagged-FP-oligonucleotide is immobilized on the surface of a QD by binding of a tag on the tagged-FP-oligonucleotide, wherein the distance between the fluorophore and the QD allows FRET.

15. A method of determining if a target entity is present in a sample comprising:
   (a) contacting the sample with a signal-off-quantum-dot-based sensor, wherein the signal-off-quantum-dot-based sensor comprises:
      an aptamer probe having a nucleotide sequence which specifically interacts with the target entity, wherein the aptamer probe is sandwiched between (a) a tagged-oligonucleotide which is capable of being immobilized on the surface of a quantum dot (QD), and (b) an oligonucleotide labeled with a fluorophore, designated as "FP-oligonucleotide," wherein when the sensor is excited by an energy source: (i) in the absence of specific interaction between the target entity and the aptamer probe, a baseline signal is emitted, and (ii) in the presence of specific interaction between the target entity and the aptamer probe, a detection signal is emitted, wherein the baseline signal is a stronger fluorescence signal than the detection signal;
   (b) contacting the sample with a quantum dot wherein the quantum dot is a FRET pair of the fluorophore;
   (c) exciting the signal-off-quantum-dot-based sensor with an energy source; and
   (d) determining the strength of emitted signal, thereby determining whether the target entity is present in the sample.

16. A method of determining if a target molecule is present in a sample comprising:
   (a) contacting the sample with a signal-on-quantum-dot-based sensor, wherein the signal-on-quantum-dot-based sensor comprises:
      an aptamer probe having a nucleotide sequence which specifically interacts with the target molecule, wherein the aptamer probe is sandwiched between (a) a quencher-labeled oligonucleotide; and (b) an oligonucleotide which is tagged and labeled with a fluorophore, designated as "tagged-FP-oligonucleotide," wherein the "tagged-FP-oligonucleotide" is capable of being immobilized on the surface of a quantum dot (QD); wherein when the sensor is excited by an energy source: (i) in the absence of specific interaction between the target entity and the aptamer probe, a baseline signal is emitted, and (ii) in the presence of specific interaction between the target entity and the aptamer probe, a detection signal is emitted, wherein the baseline signal is a weaker fluorescence signal than the detection signal;
   (b) contacting the sample with a quantum dot wherein the quantum dot is a FRET pair of the fluorophore;
   (c) exciting the signal-on-quantum-dot-based sensor with an energy source; and
   (d) determining the strength of emitted signal, thereby determining whether the target entity is present in the sample.

* * * * *

UNITED STATES PATENT AND TRADEMARK OFFICE
CERTIFICATE OF CORRECTION

PATENT NO.        : 8,642,260 B2                                Page 1 of 1
APPLICATION NO.   : 13/124356
DATED             : February 4, 2014
INVENTOR(S)       : Zhang et al.

It is certified that error appears in the above-identified patent and that said Letters Patent is hereby corrected as shown below:

IN THE CLAIMS:

Claim 8, column 17, line 31:

Reads: "in the absence"
Should read: -- (i) in the absence --

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,642,260 B2                                    Page 1 of 1
APPLICATION NO.  : 13/124356
DATED            : February 4, 2014
INVENTOR(S)      : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 224 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: Synthetic nucleotide sequence

<400> SEQUENCE: 1
```

-continued

```
tcacagatga gt                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetic nucleotide sequence

<400> SEQUENCE: 2
gtctcccgag at                                                          12

<210> SEQ ID NO 3
<211> LENGTH: 56
<212> TYPE: DNA
<213> ORGANISM: Artificial Sequence
<220> FEATURE:
<223> OTHER INFORMATION: Synthetic nucleotide sequence

<400> SEQUENCE: 3
actcatctgt gatatctcgg gagacaagga aaatccttca atgaagtggg tctccc          56

<210> SEQ ID NO 4
<211> LENGTH: 12
<212> TYPE: DNA
<213> ORGANISM: Artificial Sequence
<220> FEATURE:
<223> OTHER INFORMATION: Synthetic nucleotide sequence

<400> SEQUENCE: 4
tcacagatga gt                                                          12

<210> SEQ ID NO 5
<211> LENGTH: 12
<212> TYPE: DNA
<213> ORGANISM: Artificial Sequence
<220> FEATURE:
<223> OTHER INFORMATION: Synthetic nucleotide sequence

<400> SEQUENCE: 5
gtctcccgag at                                                          12

<210> SEQ ID NO 6
<211> LENGTH: 57
<212> TYPE: DNA
<213> ORGANISM: Artificial Sequence
<220> FEATURE:
<223> OTHER INFORMATION: Synthetic nucleotide sequence

<400> SEQUENCE: 6
actcatctgt gatatctcgg gagacaagga taaatccttc aatgaagtgg gtctccc         57
```